(12) United States Patent
Ketter et al.

(10) Patent No.: US 10,398,682 B2
(45) Date of Patent: Sep. 3, 2019

(54) METHODS AND COMPOSITIONS TO PREVENT OR TREAT BACTERIAL INFECTIONS

(71) Applicants: Patrick Ketter, San Antonio, TX (US); Bernard Arulanandam, Helotes, TX (US); M. Neal Guentzel, San Antonio, TX (US)

(72) Inventors: Patrick Ketter, San Antonio, TX (US); Bernard Arulanandam, Helotes, TX (US); M. Neal Guentzel, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/905,359

(22) PCT Filed: Jul. 15, 2014

(86) PCT No.: PCT/US2014/046656
§ 371 (c)(1),
(2) Date: Jan. 15, 2016

(87) PCT Pub. No.: WO2015/009699
PCT Pub. Date: Jan. 22, 2015

(65) Prior Publication Data
US 2016/0151333 A1    Jun. 2, 2016

Related U.S. Application Data

(60) Provisional application No. 61/846,531, filed on Jul. 15, 2013.

(51) Int. Cl.
| | | |
|---|---|---|
| *A61K 31/4164* | (2006.01) | |
| *A61K 31/4184* | (2006.01) | |
| *A61K 31/4196* | (2006.01) | |
| *A61K 31/428* | (2006.01) | |
| *A61K 31/437* | (2006.01) | |
| *A61K 31/52* | (2006.01) | |
| *A61K 31/522* | (2006.01) | |
| *A61K 31/5415* | (2006.01) | |
| *A61K 45/06* | (2006.01) | |

(52) U.S. Cl.
CPC ...... *A61K 31/4164* (2013.01); *A61K 31/4184* (2013.01); *A61K 31/4196* (2013.01); *A61K 31/428* (2013.01); *A61K 31/437* (2013.01); *A61K 31/52* (2013.01); *A61K 31/522* (2013.01); *A61K 31/5415* (2013.01); *A61K 45/06* (2013.01)

(58) Field of Classification Search
CPC ............ A61K 31/4164; A61K 31/5415; A61K 31/522; A61K 31/52; A61K 31/437; A61K 31/428; A61K 31/4196; A61K 31/4184
See application file for complete search history.

(56) References Cited

U.S. PATENT DOCUMENTS

| | | | |
|---|---|---|---|
| 6,962,151 B1 | 11/2005 | Knoch et al. | 128/200.14 |
| 8,592,468 B2 | 11/2013 | Holmgren et al. | 514/373 |
| 2010/0028334 A1 | 2/2010 | Cottarel et al. | 514/1.1 |
| 2010/0227899 A1 | 9/2010 | Billack et al. | 514/359 |
| 2011/0104308 A1 | 5/2011 | Stamler et al. | 424/708 |
| 2011/0288130 A1 | 11/2011 | Holmgren et al. | 514/338 |

FOREIGN PATENT DOCUMENTS

CA          2691692          1/2009

OTHER PUBLICATIONS

Turos et al., "Unsymmetric aryl-alkyl disulfide growth inhibitors of methicillin-resistant *Staphylococcus aureus* and *Bacillus antracis*". Bioorganic & Medicinal Chem., 16(13), 6501-6508, 2008.*
Lu et al., "Inhibition of bacterial thioredoxin reductase: an antibiotic mechanism targeting bacteria lacking glutathione". FASEB J., published online Dec. 17, 2012.*
Silasi-Mansat et al., "Complement inhibition decreases the procoagulant response and confers organ protection in a baboon model of *Escherichia coli* sepsis". Blood, vol. 116(6), pp. 1002-1010 (Year: 2010).*
International Search Report and Written Opinion issued in PCT/US2014/046656, dated Nov. 4, 2014.
International Preliminary Report on Patentability issued in PCT/US2014/046656, dated Jan. 28, 2016.
Lu et al., "Inhibition of bacterial thioredoxin reductase: an antibiotic mechanism targeting bacteria lacking glutathione", *FASEB J.*, 27(4): 1394-1403, 2013.
Kirkpatrick et al., "Mechanisms of inhibition of the thioredoxin growth factor system by antitumor 2-imidazolyl disulfides", *Biochemical Pharmacology*, 1998, vol. 55, No. 7, pp. 987-994.
Villers et al., "Nosocomial Acinetobacter baumannii infections: microbiological and clinical epidemiology", *Annals of Internal Medicine*, 1998, vol. 129, No. 3, pp. 182-189.

\* cited by examiner

*Primary Examiner* — Barbara P Badio
(74) *Attorney, Agent, or Firm* — Norton Rose Fulbright US LLP

(57) ABSTRACT

Certain embodiments are directed to methods and compositions for preventing or treating bacterial infections. In certain embodiments the compositions comprise thioredoxin inhibitors, and/or thioredoxin-like inhibitors.

4 Claims, 10 Drawing Sheets

| Bacteria | MIC (µg/mL) | MBC (µg/mL) |
| --- | --- | --- |
| CI77 | 31.25 | 31.25 |
| CI78 | 62.5 | 62.5 |
| CI79 | 31.25 | 31.25 |
| CI80 | 31.25 | 31.25 |
| CI86 | 31.25 | 31.25 |

FIG. 6

|  | MIC | | MBC | |
| --- | --- | --- | --- | --- |
| Strain | Doxycycline | PX-12 | Doxycycline | PX-12 |
| A. baumannii CI 77 | 32 | 16 | 64 | 16 |
| A. baumannii CI 78 | 1 | 32 | 8 | 32 |
| A. baumannii CI 79 | 16 | 16 | 32 | 16 |
| A. baumannii CI 80 | 8 | 16 | 32 | 16 |
| A. baumannii CI 86 | 16 | 16 | 16 | 32 |
| A. baumannii ATCC 19606 | <0.5 | 8 | 4 | 16 |
| E. coli ATCC 25922 | 1 | 16 | 32 | 16 |

METHODS AND COMPOSITIONS TO PREVENT OR TREAT BACTERIAL INFECTIONS

PRIORITY

This application is a national phase application under 35 U.S.C. § 371 of International Application No. PCT/US2014/046656, filed Jul. 15, 2014, which claims priority to U.S. Provisional Patent Application Ser. No. 61/846,531 filed Jul. 15, 2013. Priority is claim to and the entire contents of each of the above-referenced disclosures are hereby incorporated by reference.

STATEMENT REGARDING FEDERALLY FUNDED RESEARCH

This invention was made with government support under contract W911NF-11-1-0136 awarded by the Army Research Office of the US Department of Defense. The government has certain rights in the invention.

BACKGROUND

*Acinetobacter baumannii* infections account for 34% of wound infections seen in soldiers injured while fighting in the Middle East. Over the last half century, the prevalence of wound infections caused by this and other Gram-negative bacterial infections have been on the rise due to the use of antibiotics on the battlefield. Today, these organisms have become the predominant pathogens recovered from war wounds sustained by soldiers due to their natural resistance to many common antimicrobials. This has been exacerbated in the case of *Acinetobacter baumannii* through the development of multi-drug resistant (MDR) strains. Although uncommon as a gastrointestinal pathogen, colonization of the gastrointestinal tract by *Acinetobacter baumannii* has been linked to the development of MDR strains. As a result, *Acinetobacter baumannii* is of major concern, not only on the battlefield, but also in hospitals and clinics, leading many to adopt screening protocols to prevent its spread.

Because of the ability of *Acinetobacter baumannii* to colonize the gastrointestinal tract, and its prevalence in wound infections seen in soldiers overseas, the inventors questioned whether it may explain some of the symptoms reported from veterans from the Persian Gulf War suffering from Gulf War Illness (GWI). GWI is a multifactorial disease presenting with a variety of symptoms. Gastrointestinal complications have been reported in some cases of GWI. Soldiers returning from the Persian Gulf may have suffered severe trauma and developed infections caused by organisms such as *Acinetobacter baumannii*, which can be very difficult to treat due to intrinsic antibiotic resistance.

There remains a need for additional compositions and therapies for treating bacterial infections.

SUMMARY

Methods and compositions are provided that can be used to prevent or treat bacterial infections. In certain embodiments the compositions comprise thioredoxin inhibitors, and/or thioredoxin-like inhibitors. Certain aspects are directed to methods of administering anti-bacterial compositions to patients before exposure or shortly after exposure to bacterial agents. The term "shortly after" refers to administering treatment within 1, 12, 24, 36, 48, 60, or 72 hours, or 1, 2, 3, 4, 5, 6, or 7 days after suffering trauma (e.g., open wound) or presentation of gastrointestinal symptoms. Such treatment can depress the viability or virulence of bacterial agents and prevent, mitigate, or hinder infection, or the development of disease caused by these bacterial agents.

In some embodiments the bacterial agent is a Gram-negative bacterium. In some embodiments the bacterial agent is a Gram-positive bacterium. In other embodiments the bacterial agent is a bacterium that may form biofilms. In yet other embodiments the bacterial agent is an intracellular bacterium. In certain aspects a bacterium to be treated are capable of breaking down or reducing SIgA. In certain aspects the bacterial agent is an *Acinetobacter*. In a further aspect the bacterial agent is *Acinetobacter baumannii*.

Certain embodiments are directed to methods of treating or preventing *Acinetobacter baumannii* colonization or infection comprising administering a clinically effective dose of an inhibitor of the enzyme thioredoxin to a subject in need thereof. As used herein, "colonized" or "colonization" refers to the subclinical presence of bacteria in a patient, whereas "infected," "infection," or "diseased" refers to disease or an overt clinical manifestation of infection, i.e., change in structure or physiology, leading to damage in any body site. Subclinical infection is the asymptomatic presence of a bacterium in an individual that may causes illness, at least in some individuals. Since subclinical infections occur without overt signs, their existence can be identified by microbiological culture or nucleic acid detection techniques such as polymerase chain reaction. Clinical disease is an infection that presents various symptoms that can be used to diagnose infection.

In certain aspects a thioredoxin inhibitor is administered in combination with a second antimicrobial agent. The second antimicrobial agent can include, but is not limited to ampicillin-sulbactam, sulbactam alone, imipenem, ticarcillin-clavulanate, ceftazidime, colistin sulfate, polymyxin B, amikacin, gentamicin, azithromycin, doxycycline, minocycline, and tigecycline. In certain aspects a thioredoxin inhibitor is administer before, concurrently, after, before and concurrently, before and after, or concurrently and after the administration of a second antimicrobial agent.

The term "treating" or "treatment" of an infection or disease refers to ameliorating the infection (i.e., arresting the growth of the bacteria or reducing the manifestation, extent or severity of at least one of the clinical symptoms thereof). "Preventing infection" means that substantially no symptoms of infection are detected after exposure of the subject to bacteria that can cause infections.

In some embodiments compositions and methods of administering these compositions to patients are intended to be used before exposure or after exposure to bacterial agents such as *Acinetobacter baumannii*. In certain embodiments the patient has an *Acinetobacter* infection. In certain aspects the patient has an *Acinetobacter baumannii* infection. In still other aspects the patient is diagnosed with or has a high probability of being diagnosed with *Acinetobacter baumannii* infection. In some instances the patient is suspected of being exposed to *Acinetobacter baumannii* in a hospital or other medical facility. In certain aspects the patient is at risk of infection, i.e., the patient is physically located, was wounded in, or was present in a location or facility that harbors or has harbored *Acinetobacter baumannii*. In a further aspect the patient is on mechanical ventilation, has sustained traumatic injuries, and/or is burned. In certain embodiments the patient is identified as having a previous or current gastrointestinal colonization. In certain aspects the patient has been wounded. In a further aspect a patient or subject is a veterinary patient or subject, e.g., livestock such as goat, cattle, sheep; or domesticated animal such as dogs and cats.

In still other aspects the patient is diagnosed with or has a high probability of being diagnosed with *Acinetobacter baumannii* wound colonization or infection with symptoms of disease.

In still other aspects the patient is diagnosed with or has a high probability of being diagnosed with *Acinetobacter baumannii* related pneumonia.

In still other aspects the patient is diagnosed with or has a high probability of being diagnosed with *Acinetobacter baumannii* that is resistant to antibiotics or other conventional anti-microbial drugs.

Certain aspects of bacterial interaction with secretory IgA (SIgA) in the GI tract and its contribution to bacterial infection are described herein. In vitro studies by Western blot analyses, using five *Acinetobacter baumannii* clinical isolates and one ATCC strain, were performed in order to detect reduction of exogenously added SIgA following incubation for 24 hours. Supernatant material from *Acinetobacter baumannii* isolates incubated with SIgA exhibited, in dose-dependent fashion, liberation of secretory component (SC) from intact SIgA. Subsequently, SIgA mediated *Acinetobacter baumannii* colonization was evaluated in vivo by oral challenge using C57BL/6, IgA−/−, pIgR−/− KO and B-cell deficient (μMT) mice. In vivo imaging studies, following gavage with PSVUE®-794 labeled bacteria, indicated wild type mice exhibited prolonged and higher intensity signals over the course of 24 hours. Survival studies resulted in over 70% mortality in wild type mice following oral *Acinetobacter baumannii* challenge compared to less than 50% in IgA−/− mice. Additionally, breakdown of SIgA by *A. baumannii* was significantly reduced following inhibition of thiol-reductase activity. Intestinal section assays also revealed both the lack of SIgA and inhibition of disulfide reduction by *A. baumannii* significantly decreased intestinal adherence. Taken together, these results identify a link between SIgA and increased *Acinetobacter baumannii* virulence. The inventors contemplate that increased virulence, at least in part, may be mediated by the interaction between bacterium and liberated SC evidenced by increased susceptibility of wild type mice following *Acinetobacter baumannii* infection. In certain aspects the bacterium to be treated is a SIgA reducing bacterium. In a further aspect the bacterium is an *Acinetobacter, Escherichia, Streptococcus, Staphylococcus, Salmonella, Lactobacillus, Enterococcus, Clostridium, Bifidobacterium, Ruminococcus*, and the like.

*Acinetobacter baumannii* breaks down SIgA through a reductive process to separate SC from dimeric IgA. Addition of a protease inhibitor had no effect on the ability of *Acinetobacter baumannii* strains to carry out this breakdown. *Acinetobacter baumannii* appears to require IgA to effectively colonize and cause infection in the gastrointestinal tract. Lack of IgA appears to attenuate the infection resulting in faster clearance of the bacteria from the gastrointestinal tract. Gastrointestinal infection by *Acinetobacter baumannii* is attenuated in IgA and B-cell deficient mice: *Acinetobacter baumannii* still adheres to the intestinal epithelium, although in significantly reduced numbers in the absence of SIgA, suggesting that SC plays a role in *Acinetobacter baumannii* adherence.

Modulation of *A. baumannii* mRNA gene transcripts corresponding to proteins involved in disulfide bond reduction were assessed through RNAseq and was confirmed by RT-qPCR following SIgA exposure. Thioredoxin-A, a gene implicated in reduction of immunoglobulins in other bacterial systems, was assessed through RNAseq and RT-qPCR analyses and found to be up-regulated following SIgA exposure.

In some aspects, the patient may be administered a clinically relevant dose of a thioredoxin inhibitor. Administration of a thioredoxin inhibitor according to the present invention will be via any common route so long as the target tissue is available via that route in order to maximize the delivery of thioredoxin inhibitor to a site for maximum (or in some cases minimum) immune response. Administration of thioredoxin inhibitor may have a local or systemic effect. In some aspects the route of administration may be topical, enteral, or parenteral. In other aspects the route of application may be transdermal or transmucosal. In other embodiments the route of administration may be oral, rectal, gastrointestinal, sublingual, sublabial, enteral, epidural, intracerebral, intracerebroventricular, epicutaneous, intradermal, subcutaneous, nasal, intranasal, intravenous, intraarterial, intramuscular, intracardiac, intraosseous, intrathecal, intraperitoneal, intravesical, intravitreal, intracavernous, intravaginal, intrauterine or intraocular.

In certain embodiments the thioredoxin inhibitors are administered enterally. In a further aspect the inhibitors are formulated for enteric release, e.g., are coated with an enteric coating. Enteric coatings include any barrier known in the art that is applied to oral medications, food supplements, or the like that prevents the release of the active agent before it reaches the small intestine. Enteric coatings prevent the destruction of the active agent by the acidic environment of the stomach. Alternatively, an agent may be filled into capsules, which are then coated with an enteric coating. The enteric coating on the particles or capsules provides for the release of the agent in the small intestine. Suitable enteric coatings include shellac, methacrylic acid copolymers and their derivatives, cellulose acetate, styrol maleic acid copolymers, polymethacrylic acid/acrylic acid copolymer, hydroxylpropyl methyl cellulose phthalate, polyvinyl acetate phthalate, hydroxyethyl ethyl cellulose phthalate, hydroxypropyl methyl cellulose acetate succinate, cellulose acetate tetrahydrophthalate, acrylic resin, timellitate, zein, calcium alginate, fatty acids, fats, and combinations thereof, among others. Examples of suitable commercially available enteric coatings include, but are not limited to, MARCOAT® 125 from Emerson Resources, Inc. (Norristown, Pa.), EUDRAGIT® from Degussa, or Cellulose Acetate Phthalate, NF ("CAP") from Eastman Chemical Co. (Kingston, Tenn.), or the like.

Certain embodiments are directed to thioredoxin inhibitors. In certain aspects the thioredoxin inhibitor is an asymmetric disulfide, such as but not limited to 2-(sec-Butyldisulfanyl)-1H-imidazole; 2-(sec-Butyldisulfanyl)thiazole; 2-(sec-Butyldisulfanyl)pyridine; 2-(sec-Butyldisulfanyl)-3H-imidazo[4,5-c]pyridine; 2-(sec-Butyldisulfanyl)benzo[d]thiazole; 2-(sec-Butyldisulfanyl)-6-fluorobenzo[d]thiazole; 2-(sec-Butyldisulfanyl)-6-chlorobenzo[d]thiazole; 2-(sec-Butyldisulfanyl)-6-iodobenzo[d]thiazole; 4-Bromo-2-(sec-butyldisulfanyl)benzo[d]thiazole; 5-Bromo-2-(sec-butyldisulfanyl)benzo[d]thiazole; 2-(sec-Butyldisulfanyl)-6-nitrobenzo[d]thiazole; 2-(Ethyldisulfanyl)-1H-benzo[d]imidazole; 2-(tert-Butyldisulfanyl)-1H-benzo[d]imidazole; 2-(sec-Butyldisulfanyl)-1H-benzo[d]imidazole; 2-(Isopropyldisulfanyl)-1H-benzo[d]imidazole; 2-(Cyclopentyldisulfanyl)-1H-benzo[d]imidazole; 2-(Cyclohexyldisulfanyl)-1H-benzo[d]imidazole; 2-(Cyclohexyldisulfanyl)benzo[d]thiazole; 2-(Cyclohexyldisulfanyl)benzo[d]oxazole; 2-(sec-Butyldisulfanyl)-6-chloro-5-fluoro-1H-benzo[d]imidazole; 6-Chloro-2-(cyclohexyldisulfanyl)-5-fluoro-1H-benzo[d]

imidazole; 2-(sec-Butyldisulfanyl)-5-nitro-1H-benzo[d]imidazole; 2-(Cyclohexyldisulfanyl)-5-nitro-1H-benzo[d]imidazole; 2-(Cyclohexyldisulfanyl)-5-ethoxy-1H-benzo[d]imidazole; (2-(Cyclohexyldisulfanyl)-1H-benzo[d]imidazol-6-yl)(phenyl)-methanone; 2-Amino-8-(cyclohexyldisulfanyl)-7H-purin-6-ol; 8-(Cyclohexyldisulfanyl)-7H-purin-6-amine; 2-(Cyclohexyldisulfanyl)-4H-benzo[d][1,3]thiazine; 2-(Cyclohexyldisulfanyl)-5-phenyl-1H-imidazole; or 3-(Cyclohexyldisulfanyl)-5-phenyl-4H-1,2,4-triazol-4-amine. In some aspects the thioredoxin inhibitor is 1-methylpropyl 2-imidazolyl disulfide (PX-12). In a further aspect the thioredoxin inhibitor is comprised in an enteric formulation.

A thioredoxin inhibitor may be administered in a manner compatible with the formulation (e.g., liposome, time release matrix or coating, etc.), and in such amount as will be prophylactically and/or therapeutically effective. The quantity to be administered depends on the subject to be treated, including, e.g., the degree of protection or treatment desired. Suitable dosage ranges are of the order of several hundred micrograms active ingredient per treatment with a range from about 0.05 pg to 1000 mg, such as in the range from about 1 mg to 300 mg, or in the range from about 10 mg to 50 mg. Suitable regiments for initial administration and booster treatments are also variable but are typified by an initial administration followed by subsequent inoculations or other administrations. Precise amounts of active ingredient administered depend on the judgment of the practitioner and may be peculiar to each subject/patient. It will be apparent to those of skill in the art that the therapeutically effective amount of therapeutic agents of this invention will depend, inter alia, upon the administration schedule, the unit dose of antigen administered, whether thioredoxin inhibitor is administered in combination with other therapeutic agents, the immune status and health of the recipient, and the therapeutic activity of the particular thioredoxin inhibitor preparation.

Well-tolerated doses of PX-12 in humans have been reported from 9 to 226 mg/m$^2$ daily. Dose-limiting toxicities were reported as Grade 3 hypoxia and Grade 2 reversible bilateral pneumonitis at the 300 mg/m$^2$ dose level. PX-12 may be administered via a central venous catheter, and patients may be placed on low dose coumadin (1 mg/day) during therapy. PX-12 may also be dosed between 54 and 128 mg/m$^2$ administered IV over 3 hours daily for 5 days every 21 days, or at a dosage of 25 mg/kg intravenously, dissolved in 10% ethanol, 0.9% NaCl.

Prior art suggests bacterial thioredoxin inhibiting molecules e.g PX-12, only show antimicrobial response against bacteria lacking glutathione (Lu et al., 2013, *FASEB J.*, 27(4), 1394-1403; Kirkpatrick et al., 1998, *Biochemical Pharmacology*, 55, 987-994; U.S. Pat. No. 8,592,468 B2). Based on genomic sequences, *Acinetobacter baumannii* has a gene encoding for glutathione; however, molecules that inhibit thioredoxin have antimicrobial properties against this organism.

A thioredoxin inhibitor treatment may be provided in one or more "unit doses." A unit dose is defined as containing a predetermined-quantity of the composition calculated to produce the desired responses in association with its administration, i.e., the appropriate route and treatment regimen. In light of the present disclosure, the quantity to be administered, and the particular route and formulation, are within the skill of those in the clinical arts. The subject to be treated may also be evaluated, in particular, the state of the subject's immune system and the protection desired. A unit dose need not be administered as a single treatment but may include intermittent or continuous treatment over a set period of time.

The thioredoxin inhibitor, e.g., PX-12, may be prepared as injectables (e.g., liquid solutions or suspensions), or as solid forms suitable for solution in or suspension in liquid prior to administration. The preparation may be emulsified and encapsulated in liposomes. The active ingredients are often mixed with carriers that are pharmaceutically acceptable and compatible with the active ingredient.

The term "pharmaceutically acceptable carrier" refers to a carrier that does not cause an allergic reaction or other untoward effect in subjects to whom it is administered. Suitable pharmaceutically acceptable carriers include, for example, one or more of water, saline, phosphate buffered saline, dextrose, glycerol, ethanol, or the like and combinations thereof. In addition, if desired, the compositions can contain minor amounts of auxiliary substances such as wetting or emulsifying agents, and/or pH buffering agents, which enhance the effectiveness of the compositions.

In some embodiments, methods further comprise testing the patient for *Acinetobacter baumannii* infection or diagnosing a patient with *Acinetobacter baumannii* infection. Additional methods may also involve treating a patient with other *Acinetobacter baumannii* treatments such as standard antibiotic treatments.

Other embodiments of the invention are discussed throughout this application. Any embodiment discussed with respect to one aspect applies to other aspects as well and vice versa. Each embodiment described herein is understood to be embodiments that are applicable to all aspects of the invention. It is contemplated that any embodiment discussed herein can be implemented with respect to any device, method, or composition, and vice versa. Furthermore, systems, compositions, and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

(FIG. 1A) A mixture of *A. baumanuii* strain CI 79 was prepared in three concentrations $10^7$, $10^6$, and $10^5$ CFU/mL-to determine whether SIgA breakdown was dose dependent with respect to bacterial concentration. (FIG. 1B) Although a reduction of SIgA degradation by *P. aeruginosa* was seen following incubation with a protease inhibitor, no difference was observed with any of the other strains tested suggesting *A. baumannii* utilized a process that was not proteolytic in nature to break down SIgA. Dithionitrobenzoic Acid and PX-12 inhibitors completely ablated SIgA reduction (FIG. 1C) and SC liberation (FIG. 1D) 2 hours after incubation at concentrations of 1 mM and 15 µg/mL, respectively.

(FIG. 3A) shows the full body in vivo live imaging showing prolonged fluorescence in WT mice at all observation points. (FIG. 3B) Region of interest (ROI) analysis confirming visual differences in mean fluorescence intensities associated with WT mice compared to lgA$^{-/-}$ and µMT mice. (FIG. 3C) Intestinal sections show reduced bacterial adherence in sections from IgA$^{-/-}$ mice compared to WT.

FIG. 6 shows the antimicrobial effect of PX-12 on *Acinetobacter baumannii*.

FIG. 10 shows a repeat minimum inhibitory concentration (MIC) experiment performed to CLSI standards: Mueller Hinton broth cation adjusted (Ca$^{++}$ 25 mg/L, Mg$^{++}$ 12.5 mg/L), bacterial concentration reduced to ~5×10$^5$ CFU/mL, compound concentrations tested range from 64 to 0.5 µg/mL, low MIC combined with low MBC indicates PX-12 compound has bactericidal activity.

DESCRIPTION

Figures 1A, 1B, 1C, 1D:
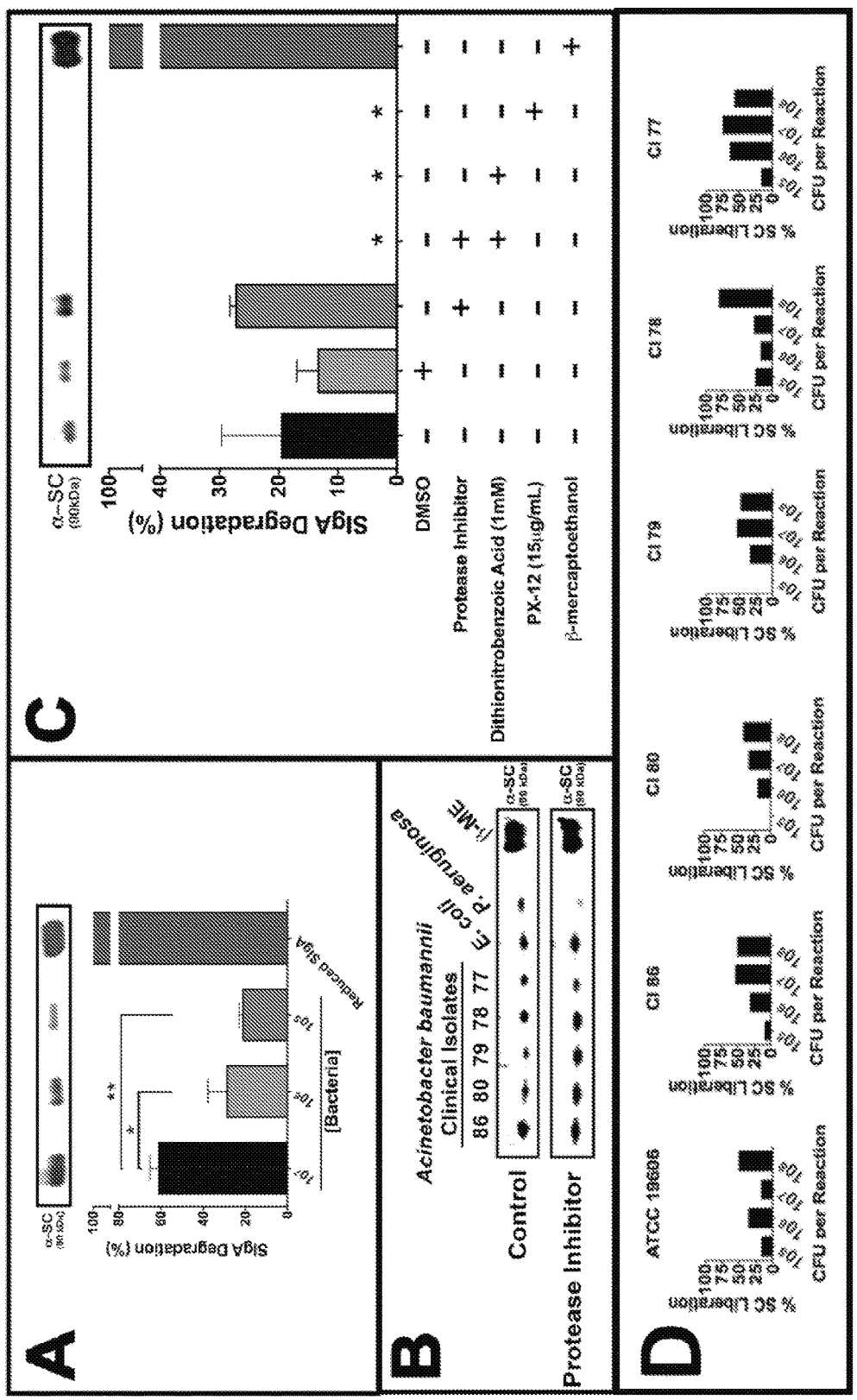
FIGS. 1A-1D shows *Acinetobacter baumannii* dissociates Secretory Component (SC) from SIgA through a reductive process.

Immunoglobulin A (IgA) is an antibody that plays a critical role in mucosal immunity. IgA can exist in a dimeric form, which is called secretory IgA (SIgA). In its secretory form, IgA is the main immunoglobulin found in mucosal secretions, including tears, saliva, colostrum and secretions from the genitourinary tract, gastrointestinal tract, prostate and respiratory epithelium. The secretory component of SIgA protects the immunoglobulin from being degraded by proteolytic enzymes, thus SIgA can survive in the harsh gastrointestinal tract environment and provide protection against microbes that multiply in body secretions. Case studies and recent literature suggest a potential link between gastrointestinal (GI) colonization and acquired antimicrobial resistance potentially following *Acinetobacter baumannii* breakdown of SIgA. Breakdown of SIgA has been shown to have an immunosuppressive effect, due to the liberation of secretory component (SC) from SIgA and subsequent inhibition of neutrophil recruitment (Mantis et al. Annals of Internal Medicine, 1998. 129(3):182-189). The breakdown of SIgA also aids bacteria in colonization of the intestinal epithelium. The inventors have conducted studies to investigate how *Acinetobacter baumannii* breaks down SIgA and what affect this has on the virulence of the organism in vivo. The data show that SIgA breakdown by *Acinetobacter baumannii* is a reductive process, rather than a proteolytic, and is significantly reduced after addition of the thioredoxin colorimetric substrate DTNB, suggesting it is acting as a competitive inhibitor.

I. Thioredoxin and Thioredoxin Inhibitors

Thioredoxin plays a role in promoting eukaryotic cell survival, proliferation, and tumor angiogenesis, which makes it an attractive molecular target for therapeutic intervention in cancer. PX-12 (1-methylpropyl 2-imidazolyl disulfide) is a thioredoxin inhibitor that irreversibly binds rendering thioredoxin redox inactive and is being investigated as a potential cancer treatment.

The thioredoxin superfamily of proteins is characterized by a motif known as a thioredoxin fold (-C-X-X-C-) which serves as the active site of the enzyme. One of the cysteine residues forms a disulfide bond with disulfide substrate, resulting in reduction and release of one half of the molecule (which can either be an organic molecule containing a disulfide linkage or sulfur containing amino acid of an adjacent protein). The second cysteine residue of the active site then forms a disulfide bond with the first resulting in reduction of the other half of the substrate. Substrates for the above enzymes, such as asymmetric disulfide compounds, of which include but are not limited to compounds such as the imidazole disulfide PX-12, act as a substrate to these enzymes and can consequently reversibly inhibit these enzymes in a competitive fashion. In the case of thioredoxin, specifically, a third cysteine residue, Cys$^{73}$, involved in dimerization of the enzyme can also act upon imidazole disulfide compounds. Doing so, however, may result in irreversible modification of the cysteine residue and prevent dimerization of the enzyme, a process necessary to reduce the enzyme back into its active state.

In certain aspects the thioredoxin inhibitor is an asymmetric disulfide, such as but not limited to 2-(sec-Butyldisulfanyl)-1H-imidazole; 2-(sec-Butyldisulfanyl)thiazole; 2-(sec-Butyldisulfanyl)pyridine; 2-(sec-Butyldisulfanyl)-3H-imidazo[4,5-c]pyridin; 2-(sec-Butyldisulfanyl)benzo[d]thiazole; 2-(sec-Butyldisulfanyl)-6-fluorobenzo[d]thiazole; 2-(sec-Butyldisulfanyl)-6-chlorobenzo[d]thiazole; 2-(sec-Butyldisulfanyl)-6-iodobenzo[d]thiazole; 4-Bromo-2-(sec-butyldisulfanyl)benzo[d]thiazole; 5-Bromo-2-(sec-butyldisulfanyl)benzo[d]thiazole; 2-(sec-Butyldisulfanyl)-6-nitrobenzo[d]thiazole; 2-(Ethyldisulfanyl)-1H-benzo[d]imidazole; 2-(tert-Butyldisulfanyl)-1H-benzo[d]imidazole; 2-(sec-Butyldisulfanyl)-1H-benzo[d]imidazole; 2-(Isopropyldisulfanyl)-1H-benzo[d]imidazole; 2-(Cyclopentyldisulfanyl)-1H-benzo[d]imidazole; 2-(Cyclohexyldisulfanyl)-1H-benzo[d]imidazole; 2-(Cyclohexyldisulfanyl)benzo[d]thiazole; 2-(Cyclohexyldisulfanyl)benzo[d]oxazole; 2-(sec-Butyldisulfanyl)-6-chloro-5-fluoro-1H-benzo[d]imidazole; 6-Chloro-2-(cyclohexyldisulfanyl)-5-fluoro-1H-benzo[d]

imidazole; 2-(sec-Butyldisulfanyl)-5-nitro-1H-benzo[d]imidazole; 2-(Cyclohexyldisulfanyl)-5-nitro-1H-benzo[d]imidazole; 2-(Cyclohexyldisulfanyl)-5-ethoxy-1H-benzo[d]imidazole; (2-(Cyclohexyldisulfanyl)-1H-benzo[d]imidazol-6-yl)(phenyl)-methanone; 2-Amino-8-(cyclohexyldisulfanyl)-7H-purin-6-ol; 8-(Cyclohexyldisulfanyl)-7H-purin-6-amine; 2-(Cyclohexyldisulfanyl)-4H-benzo[d][1,3]thiazine; 2-(Cyclohexyldisulfanyl)-5-phenyl-1H-imidazole; or 3-(Cyclohexyldisulfanyl)-5-phenyl-4H-1,2,4-triazol-4-amine. In some aspects the thioredoxin inhibitor is 1-methylpropyl 2-imidazolyl disulfide (PX-12).

II. Acinetobacter

Acinetobacter is a genus of Gram-negative bacteria belonging to the Gammaproteobacteria. Acinetobacter spp. are non-motile and oxidase-negative, and occur in pairs under magnification. They are important soil organisms, where they contribute to the mineralization of, for example, aromatic compounds. Acinetobacter spp. are a source of infection in debilitated patients in the hospital, in particular the species Acinetobacter baumannii.

Species of the genus Acinetobacter are aerobic non-fermentative Gram-negative bacilli. They typically show coccobacillary morphology on nonselective agar. Rods predominate in fluid media, especially during early growth. Most strains of Acinetobacter, except some of the A. lwoffii strain, grow well on MacConkey agar (without salt). Although officially classified as nonlactose-fermenting, they are often partially lactose-fermenting when grown on MacConkey agar. They are oxidase-negative, nonmotile, and usually nitrate negative. Bacteria of the genus Acinetobacter are known to form intracellular inclusions of polyhydroxyalkanoates under certain environmental conditions.

FIG. 1 shows Acinetobacter baumannii dissociates Secretory Component (SC) from SIgA through a reductive process. Acinetobacter baumannii was incubated with 50 µg/mL SIgA to examine breakdown of the immunoglobulin. Breakdown of SIgA by A. baumannii was observed by liberation of secretory component from dimeric IgA. Goat anti-human secretory component (free and bound) antibody was used to monitor this occurrence though Western blot. A mixture of A. baumannii strain CI 79 was prepared in three concentrations—$10^7$, $10^6$, and $10^5$ CFU/mL—to determine whether SIgA breakdown was dose dependent with respect to bacterial concentration FIG. 1A. Previous literature examining SIgA degradation by Gram-negative pathogens suggested this process was proteolytic in nature so previous experiments were repeated with a single inoculum (~$10^7$ CFU/mL) of each A. baumannii clinical isolate in our bacterial library along with E. coli (strong reductase) and P. aeruginosa (known IgA protease) in the presence or absence of protease inhibitor. Although a reduction of SIgA degradation by P. aeruginosa was seen following incubation with protease inhibitor, no difference was observed with any of the other strains tested suggesting A. baumannii utilized a process that was not proteolytic in nature to break down SIgA FIG. 1B. Next, two competitive inhibitors of reductase enzymes targeting the thioredoxin fold (-C-X-X-C-) motif typically found in thiol-reductase enzymes (thioredoxin, glutathione, thioredoxin reductase, etc) were identified. The first, dithionitrobenzoic acid (Ellman's reagent) is often used as a colorimetric substrate to monitor thioredoxin activity as it produces a bright yellow color upon cleavage of the disulfide bond within the molecule. The second is PX-12. Both of these inhibitors completely ablated SIgA reduction and SC liberation 2 hours after incubation at concentrations of 1 mM and 15 µg/mL, respectively (FIG. 1C). Although not shown here, inhibition was still evident at 24 hours with Ellman's reagent, PX-12 inhibition seemed to be overcome by the bacteria after about 12 hours. This may suggest that either the bacteria are producing more reductase enzyme eventually overwhelming the concentrations of PX-12 in the mixture, or the observed PX-12 inhibition is not irreversible with respect to the bacterial reductase. (Error bars represent±SEM in all graphs; statistical differences determined by ANOVA with Dunnett correction; *significance $p<0.01$; **$p<0.001$).

Figure 2:
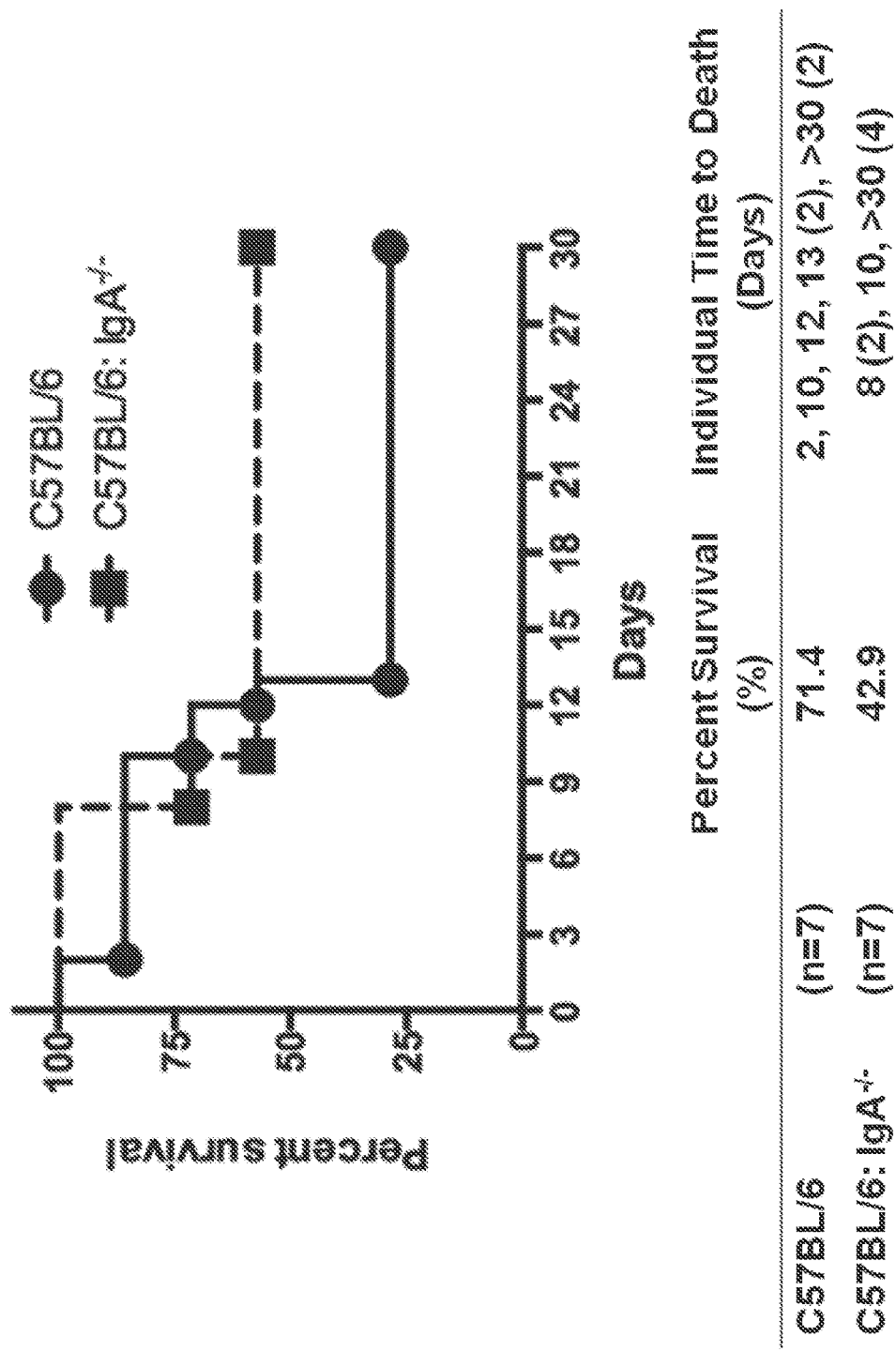
FIG. 2 shows IgA enhances virulence of *Acinetobacter baumannii* during GI challenge.

FIG. 2 shows IgA enhances virulence of Acinetobacter baumannii during GI challenge. Wild type (WT) and IgA deficient ($IgA^{-/-}$) C57BL/6 mice were challenged with $5 \times 10^7$ CFU by oral gavage and monitored for morbidity and mortality over the course of a month. 71% of WT mice challenged succumbed to infection compared to only 43% of $IgA^{-/-}$ mice indicating IgA is necessary for virulence of Acinetobacter baumannii during GI challenge (data representative of three independent experiments).

Figures 3A, 3B, 3C:
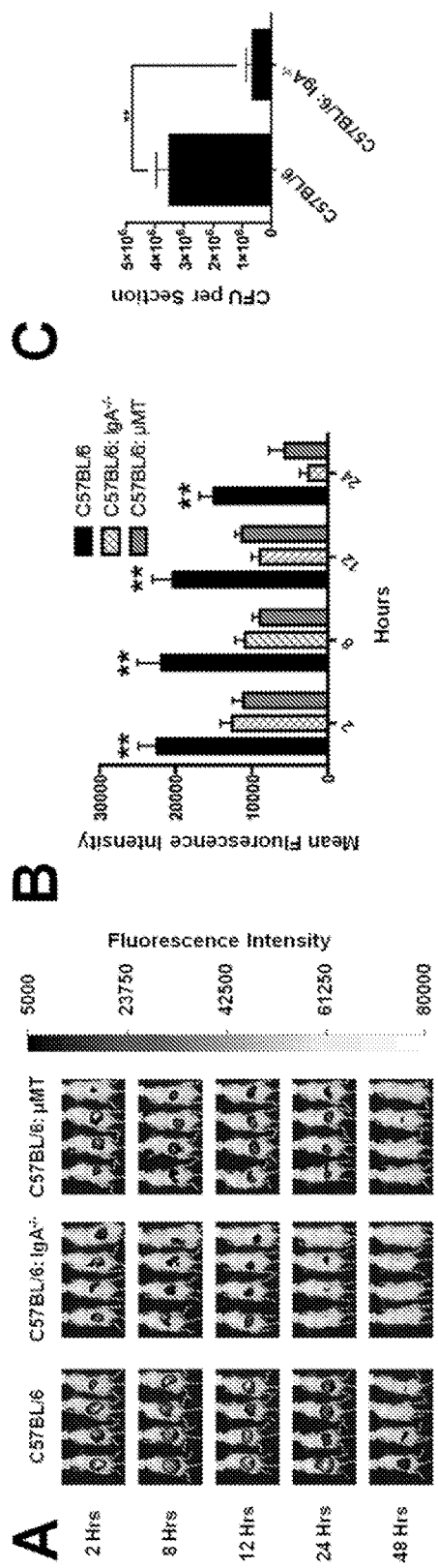
FIGS. 3A-3C shows IgA enhances *Acinetobacter baumannii* adherence and colonization in the GI tract.

FIG. 3 shows IgA enhances Acinetobacter baumannii adherence and colonization in the GI Tract. Acinetobacter baumannii was stained with the cationic dye PSVUE®-794, a near-infrared fluorescent dye, and used to track progression of Acinetobacter baumannii through the GI tract following oral gavage. Wild type (WT), IgA deficient ($IgA^{-/-}$), and B-cell deficient (µMT) mice were challenged with $5 \times 10^7$ CFU of the stained bacteria and monitored over the course of two days by full body in vivo live imaging showing prolonged fluorescence in WT mice at all observation points (A). Region of interest (ROI) analysis confirmed these visual differences with significant differences ($p<0.001$) in mean fluorescence intensities associated with WT mice compared to $IgA^{-/-}$ and µMT mice at all observation points (B). Intestinal sections obtained from infant mice also show significantly ($p<0.001$) reduced bacterial adherence in sections from $IgA_{-/-}$ mice compared to WT (C).

Figure 4:
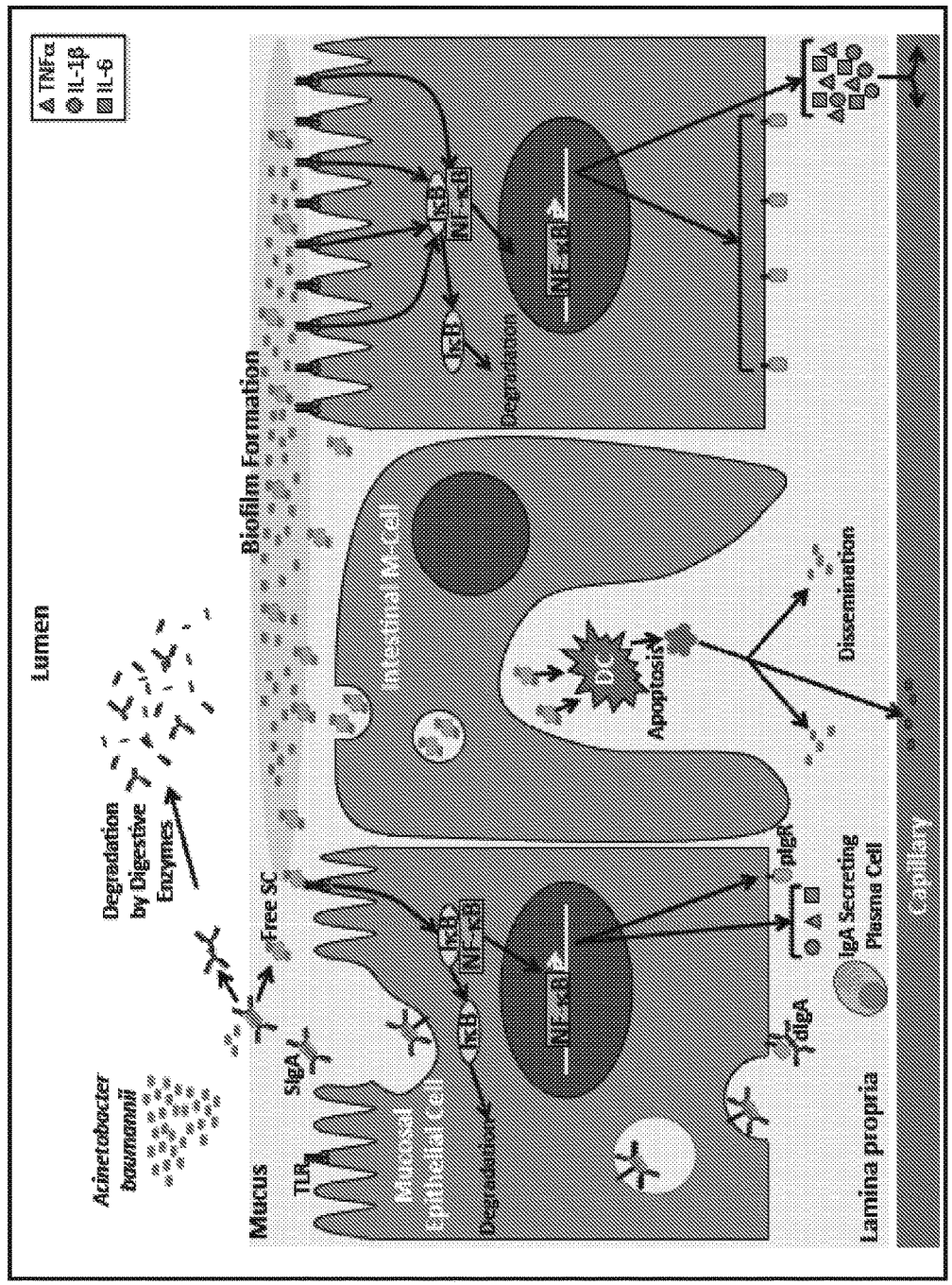
FIG. 4 is a working model of *Acinetobacter baumannii* gastrointestinal infection.

FIG. 4 is a working model of Acinetobacter baumannii gastrointestinal infection. Dimeric IgA is produced by IgA secreting plasma cells at the lamina propria of the intestinal epithelium. The polymeric immunoglobulin receptor (pIgR) has high affinity for the J-chain of polymeric immunoglobulins and binds covalently to dimeric IgA. Binding facilitates translocation of the immunoglobulin to the intestinal lumen where pIgR is cleaved and released forming SIgA. During Acinetobacter baumannii infection, the bacteria reduce the bonds between the dimeric IgA and SC (the remnant of pIgR still bound to IgA) to form free SC. The unprotected IgA then becomes susceptible to degradation by digestive enzymes while free SC binds to Acinetobacter baumannii in a non-specific manner to form immune complexes with the bacteria. These complexes allow the non-motile bacterium to anchor itself within the mucous lining. In so doing, the bacteria can colonize and form biofilms within the gastrointestinal tract. Biofilm formation at the luminal surface of the enterocyte may result in increased TLR activation to stimulate NF-kB activation resulting in increased pro-inflammatory cytokine release and pIgR expression at the basal surface of the cell to allow for increased SIgA. Additionally, the immune complexes formed may be transcytosed by intestinal M-cells for presentation to dendritic cells (DC). If the bacteria are present in high enough numbers, bacterial outer membrane proteins may cause apoptosis in the DCs allowing the bacteria to disseminate into the body.

Figure 5:
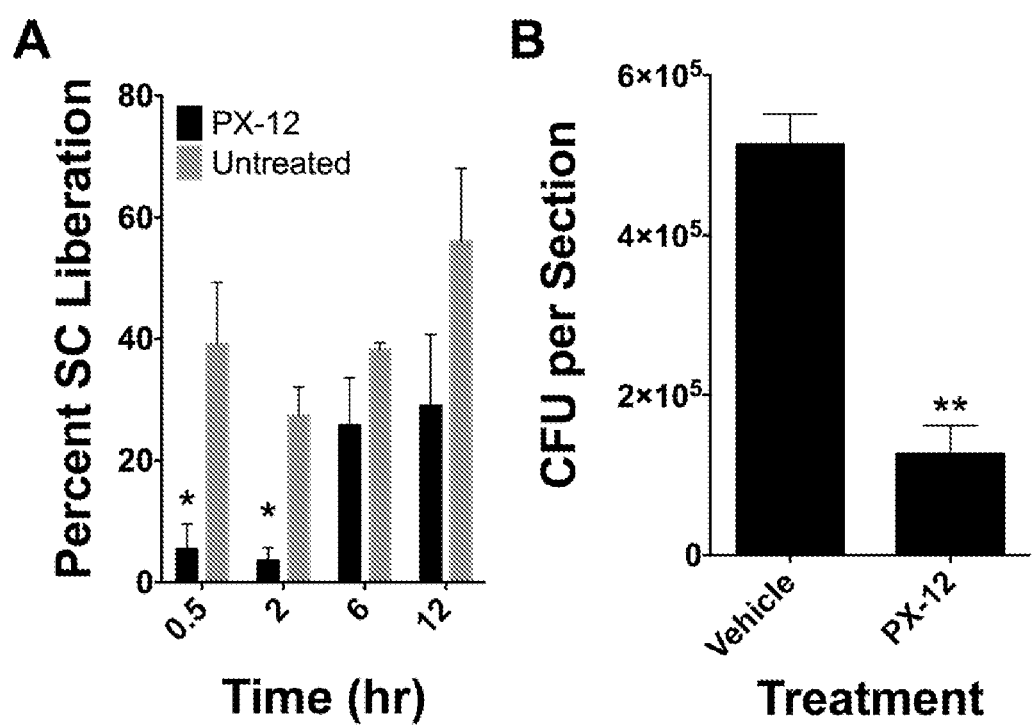
FIG. 5 shows SIgA reduction and intestinal adhesion by *Acinetobacter baumannii* inhibited by thioredoxin inhibitor PX-12.

FIG. 5 shows SIgA breakdown and intestinal adhesion by Acinetobacter baumannii is inhibited by thioredoxin Inhibitor PX-12. SIgA breakdown by *Acinetobacter baumannii* is significantly reduced up to 2 hours following treatment with 18 μg/mL PX-12 (A). This same dose significantly inhibits bacterial adherence to intestinal sections obtained from WT C57BL/6 mice (B).

FIG. 6 shows the antimicrobial effect of PX-12 on *Acinetobacter baumannii*. Initial experiments with PX-12 examining the effect of PX-12 on SIgA reduction by *A. buamannii* revealed unexpected results with respect to bacterial growth. PX-12 concentrations used in these experiments approximated the concentration reported "well tolerated" by mice (~500 μg/mouse; 500 μg/mL for this experiment). This dose resulted in a visible decrease in bacterial pellet size when supernatant was collected for analysis. After performing a minimum inhibitor concentration (MIC) determination, the inventors discovered that the MIC for PX-12 with respect to the multi-drug resistant (MDR) *Acinetobacter baumanniii* clinical isolates, with one exception, was 31.25 μg/mL. Furthermore, this concentration was also bactericidal leading us to believe it may potentially be useful as a new antimicrobial compound for treating MDR *Acinetobacter baumannii*. (Bacterial concentrations used in presented studies ~100× higher than recommended by CLSI standards)

Figure 7:
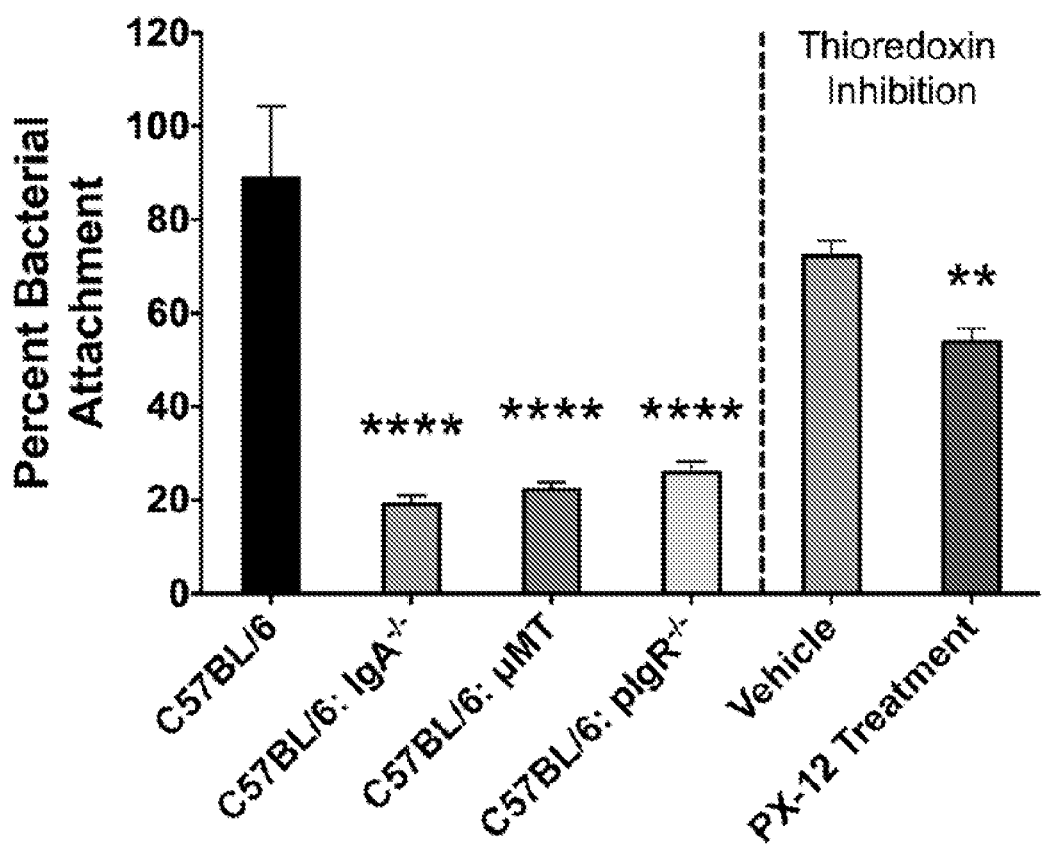
FIG. 7 shows treatment with the mammalian thioredoxin-1 inhibitor PX-12 significantly reduced bacterial attachment by 40%.

FIG. 7 shows sections of small intestine (mostly duodenal/ileal) from infant WT, IgA$^{-/-}$, pIgR$^{-/-}$, and μMT mice. Intestinal sections were cut down one side to expose the inner lumen of the intestine and individually placed in suspensions of *A. baumannii* strain CI 79 ($10^7$ CFU/mL). The sections were incubated in this mixture for 30 minutes, washed twice in 250 volumes of sterile PBS and soaked in 500 volumes of PBS (volume of section ~50-100 μL) for five minutes. The remaining bound bacteria were enumerated through homogenization of each section into single cell suspensions in 10 mL sterile PBS followed by dilution plating. Using the intestinal sections collected from WT mice as the 100% control, nearly 80% reductions in bacterial adherence were observed in IgA deficient intestinal sections obtained from IgA$^{-/-}$, pIgR$^{-/-}$, and μMT mice compared to WT. Additionally, treatment with the mammalian thioredoxin-1 inhibitor PX-12 also significantly reduced bacterial attachment by ~40%.

Figure 8:
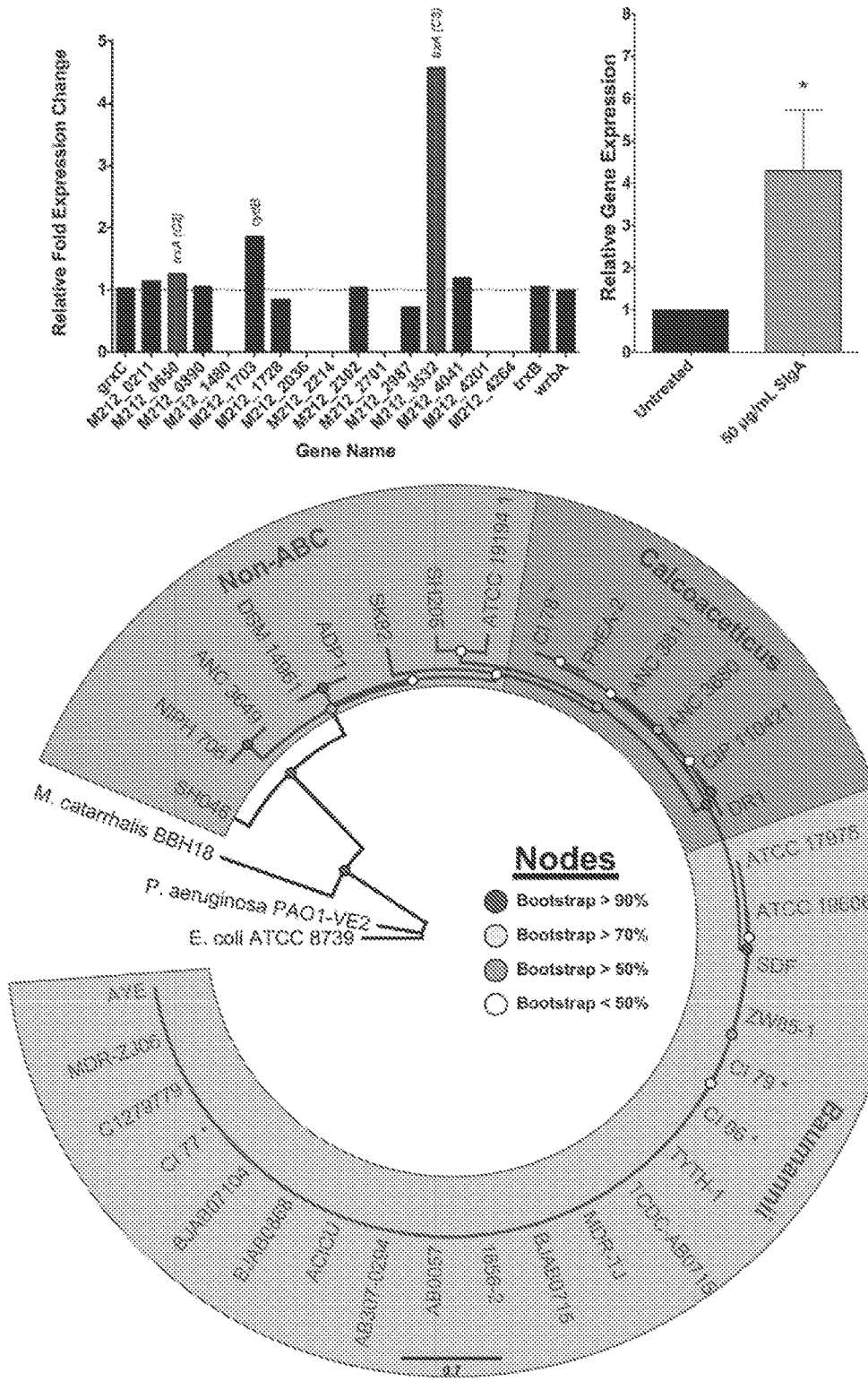
FIG. 8 shows thioredoxin as a mediator of SIgA breakdown

FIG. 8 shows thioredoxin as a mediator of SIgA breakdown. Although inhibition of SIgA reduction was observed with compounds such as dithionitrobenzoic acid and PX-12, both known substrates of thiol-reducing enzymes, there are many *A. baumannii* enzymes classified as reductases. In order to narrow this list of potential mediators of SIgA reduction, RNA sequencing on *A. baumannii* strain CI 79 was performed. The transcriptome expression profile for *A. baumannii* treated for 1 hour with SIgA against untreated *A. baumannii* was assessed using Ion Torrent Personal Genomics Machine (PGM). Eighteen genes involved in reduction-oxidization reactions, based on gene ontology (GO) classifications, were identified and examined for fold change difference in gene expression following SIgA exposure. Of these 18 genes, only one exhibited a fold change greater than 2 following SIgA exposure. This gene, M212_3532, was annotated as thioredoxin-A (trxA), the bacterial homologue to mammalian thioredoxin-1. Although, not as greatly modulated, M212_0650, also annotated as trxA, exhibited increased gene expression (>1). Based on these data, trxA gene expression was examined by quantitative reverse transcription polymerase chain reaction (qRT-PCR) over time. Significantly increased gene expression of trxA (~4.5 fold) 2 hours after exposure to SIgA by the $2^{-\Delta\Delta ct}$ method was observed (FIG. 8B). Subsequently gene sequences corresponding to trxA in 34 *Acinetobacter* spp. isolates were extracted and assessed for phylogenetic relatedness by PhymL following ClustalW alignment utilizing Geneious analysis software. The resulting phylogenetic tree with corresponding bootstrap values indicated a very high level of genetic conservation between *Acinetobacter* spp. with respect to the thioredoxin-A gene sequence (FIG. 8C). In fact, within the Baumannii clade there was nearly 100% sequence homology between strains. Other clades include Calcoaceticus, and non-*A. baumannii-calcoaceticus* (non-ABC). (Error bars represent±SEM (C); statistical difference determined by Welch t-test; *significance p<0.01)

Figure 9:
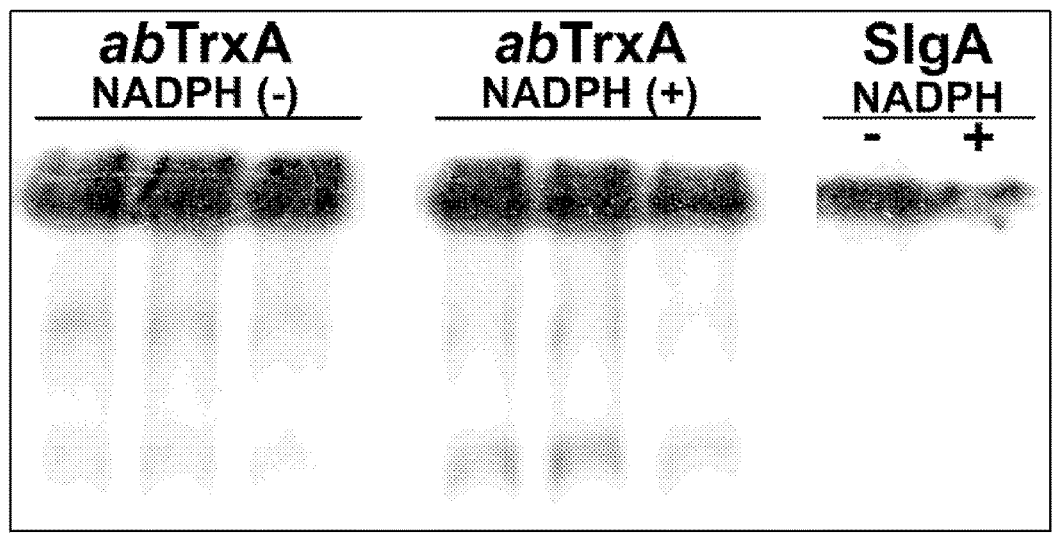
FIG. 9 shows reduction of SIgA by recombinant *A. baumannii* thioredoxin A (abTrxA).

FIG. 9 shows reduction of SIgA by recombinant *A. baumannii* thioredoxin-A (abTrxA). Recombinant abTrxA derived from *A. baumannii* clinical isolate CI 79 was expressed in Rosetta *E. coli* cells and purified using an amylose resin column. Following elution of the protein with maltose, *E. coli* derived thioredoxin reductase (ecTrxB) was found to have eluted with the purified protein. As a result, although reduction of SIgA was observed in the absence of NADPH (left), reduction of SIgA was enhanced with addition of 400 μM NADPH (center). NADPH had no effect on SIgA in the absence of recombinant protein (right). This pattern of SIgA reduction was identical to that observed with bacteria alone.

III. Compositions and Formulations

The compounds described herein can be comprised in a variety of formulations, including for oral, or topical delivery (e.g., administered orally, parenterally, by inhalation spray, nebulizer, topically, rectally, nasally, buccally). The compounds described herein can, for example, be administered by injection intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.001 to about 100 mg/kg of body weight, e.g., between 0.001-1 mg/kg, 1-100 mg/kg, or 0.01-5 mg/kg, every 4 to 120 hours, e.g., about every 6, 8, 12, 24, 48, or 72 hours, or according to the requirements of the particular compound. The methods herein contemplate administration of an effective amount of compound or compound composition to achieve the desired or stated effect. Typically, the pharmaceutical compositions of this invention will be administered from about 1 to about 6 times per day. Alternatively, the compounds can be administered as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Pharmaceutical compositions of this invention comprise a compound described herein or a pharmaceutically acceptable salt thereof; an additional compound including for example, a steroid or an analgesic; and any pharmaceutically acceptable carrier, adjuvant or vehicle. The compositions delineated herein include the compounds described herein, as well as additional therapeutic compounds (e.g., antibiotics, other antimicrobials, or probiotics) if present, in amounts effective for achieving a modulation of disease or disease symptoms.

The compositions are generally made by methods including the steps of combining a compound described herein with one or more carriers and, optionally, one or more additional therapeutic compounds delineated herein.

The term "pharmaceutically acceptable carrier" refers to a carrier that may be administered to a patient, together with a compound of this invention, and which does not destroy the pharmacological activity thereof and is nontoxic when administered in doses sufficient to deliver a therapeutic amount of the compound.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase which can be combined with emulsifying and/or suspending agents. If desired, certain sweetening and/or flavoring and/or coloring agents may be added.

In certain embodiment thioredoxin inhibitors can be formulated for controlled delivery or release. Thioredoxin inhibitor formulations can be coated to modify the release properties of the composition, such as with a delayed release coating, sustained release coating, controlled release coating, targeted release coating, enteric coating, and the like, or combinations thereof. The coating may further comprise lecithin, which serves as an anti-sticking agent. Preferably, the coating is an enteric coating. Enteric coatings include any barrier known in the art that is applied to oral medications, food supplements, or the like that prevents the release of the active agent before it reaches the small intestine. Enteric coatings prevent the destruction of the active agent by the acidic environment of the stomach. Typically, enteric coatings are stable at very acidic pH, such as in the stomach, and break down rapidly in mildly acidic or higher pH, such as in the small intestine. Suitable enteric coatings include, but are not limited to a shellac, such as MARCOAT® 125 from Emerson Resources, Inc. (Norristown, Pa.), methacrylic acid copolymers and their derivatives, such as EUDRAGIT® from Degussa, cellulose acetate, such as Cellulose Acetate Phthalate, NF ("CAP") from Eastman Chemical Co. (Kingston, Tenn.), styrol maleic acid copolymers, polymethacrylic acid/acrylic acid copolymer, hydroxylpropyl methyl cellulose phthalate, polyvinyl acetate phthalate, hydroxyethyl ethyl cellulose phthalate, hydroxypropyl methyl cellulose acetate succinate, cellulose acetate tetrahydrophthalate, acrylic resin, trimellitate, zein, calcium alginate, fatty acids, fats, and combinations thereof, among others.

The enteric coating is formed or deposited on the exterior surfaces of a particle in a manner in which the enteric coating substantially encapsulates a particle. "Encapsulation" or equivalent language means the enteric coating formed on the particles covers essentially the entire outer surface of the particles. The extent of encapsulation by the enteric coating must be sufficient such that the active agents are not overly exposed immediately to the gastric juices of the stomach upon consumption.

Preferably, the coating is of uniform thickness to provide substantially a uniform rate of release among the particles. Generally, "uniform thickness" is intended to mean that the thickness of the coating does not vary more than about 50 percent, and preferably not more than about 25 percent. The coating is generally applied to provide a coating of about 10 to about 40 percent based on the weight of the dried particles.

In one embodiment, the particles are coated with an enteric coating composition by suspending the particles in a fluid bed and spraying them with the coating composition, followed by drying, and recovering the coated particles. Such fluid bed coating systems can include top spray systems, bottom spray systems, tangential (rotor) spray systems, and the like. Suitable multi-purpose fluid bed processors also are generally known for particle coating applications that enable different types of spray nozzle inserts to be readily installed in a common spray system, so that the same processor can be operated to apply a coating variously as a top spray, Wurster spray, or tangential spray. A coating system comprising a rotary drum coater also could be used. Of course, other coating or application systems, including coextrusion and film processing, could also be used. These coating processes can be run continuously or batch style.

Upon ingestion or placement in a very low pH environment (such as in gastric juice in the stomach), the enteric coating does not readily dissolve. Instead, the enteric coating dissolves at a higher pH, such as in the small intestine. As the enteric coating begins to dissolve, the thioredoxin inhibitor is released.

The enteric-coated particles of the invention may be formulated into a variety of compositions, such as compressed tablets, pills, capsules, lozenges, pharmaceuticals, or the like. In one particular aspect, the enteric-coated particles of the invention can be further processed into tablets by combining the particles with conventional tablet binders, such as starch, gelatin, sugar (such as glucose, fructose, lactose, and the like), or mixtures thereof. The tablet binders should be food grade or pharmaceutically-acceptable ingredients.

The compounds of this invention may be administered by aerosol, nebulizer, or inhalation. In some embodiments, the composition is in the form of a dry powder, a suspension, or a solution. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Exemplary methods and devices for aerosol or inhalation include those described in U.S. Pat. No. 6,962,151, which is incorporated herein by reference in its entirety.

Compositions formulated for inhaled delivery generally include particles having a mean diameter of from about 0.1 µm to about 50 µm (e.g., from about 0.1 µm to about 10 µm, or from about 0.2 µm to about 5 µm). In some embodiments, the composition includes a dispersion of suitably-sized dry particles, for example, precipitants or crystals or a dispersion of a solution (e.g., droplets) of a suitable size.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The disclosed compositions and method of use are generally described, with examples incorporated as particular embodiments and to demonstrate the practice and advantages thereof. It is understood that the examples are given by way of illustration and are not intended to limit the specification or the claims in any manner. It will be understood that embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific device and method of use described herein. Such equivalents are considered to be within the scope of this invention and are covered by the claims.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

What is claimed is:

1. A method of treating or mitigating bacterial colonization or infection in a subject comprising administering a clinically effective dose of an asymmetric disulfide thioredoxin inhibitor to a subject at risk of exposure to *Acinetobacter*.

2. The method of claim 1, wherein the asymmetric disulfide thioredoxin inhibitor is 2-(sec-Butyldisulfanyl)-1H-imidazole; 2-(sec-Butyldisulfanyl)thiazole; 2-(sec-Butyldisulfanyl)pyridine; 2-(sec-Butyldisulfanyl)-3H-imidazo[4,5-c]pyridine; 2-(sec-Butyldisulfanyl)benzo[d]thiazole; 2-(sec-Butyldisulfanyl)-6-fluorobenzo[d]thiazole; 2-(sec-Butyldisulfanyl)-6-chlorobenzo[d]thiazole; 2-(sec-Butyldisulfanyl)-6-iodobenzo[d]thiazole; 4-Bromo-2-(sec-butyldisulfanyl)benzo[d]thiazole; 5-Bromo-2-(sec-butyldisulfanyl)benzo[d]thiazole; 2-(sec-Butyldisulfanyl)-6-nitrobenzo[d]thiazole; 2-(Ethyldisulfanyl)-1H-benzo[d]imidazole; 2-(tert-Butyldisulfanyl)-1H-benzo[d]imidazole; 2-(sec-Butyldisulfanyl)-1H-benzo[d]imidazole; 2-(Isopropyldisulfanyl)-1H-benzo[d]imidazole; 2-(Cyclopentyldisulfanyl)-1H-benzo[d]imidazole; 2-(Cyclohexyldisulfanyl)-1H-benzo[d]imidazole; 2-(Cyclohexyldisulfanyl)benzo[d]thiazole; 2-(Cyclohexyldisulfanyl)benzo[d]oxazole; 2-(sec-Butyldisulfanyl)-6-chloro-5-fluoro-1H-benzo[d]imidazole; 6-Chloro-2-(cyclohexyldisulfanyl)-5-fluoro-1H-benzo[d]imidazole; 2-(sec-Butyldisulfanyl)-5-nitro-1H-benzo[d]imidazole; 2-(Cyclohexyldisulfanyl)-5-nitro-1H-benzo[d]imidazole; 2-(Cyclohexyldisulfanyl)-5-ethoxy-1H-benzo[d]imidazole; (2-(Cyclohexyldisulfanyl)-1H-benzo[d]imidazol-6-yl)(phenyl)-methanone; 2-Amino-8-(cyclohexyldisulfanyl)-7H-purin-6-ol; 8-(Cyclohexyldisulfanyl)-7H-purin-6-amine; 2-(Cyclohexyldisulfanyl)-4H-benzo[d][1,3]thiazine; 2-(Cyclohexyldisulfanyl)-5-phenyl-1H-imidazole; or 3-(Cyclohexyldisulfanyl)-5-phenyl-4H-1,2,4-triazol-4-amine.

3. The method of claim 1, wherein the asymmetric disulfide thioredoxin inhibitor is 1-methylpropyl 2-imidazolyl disulfide (PX-12).

4. The method of claim 1, wherein the asymmetric disulfide thioredoxin inhibitor is formulated in a controlled release formulation.

* * * * *